United States Patent
Laredo et al.

(10) Patent No.: US 8,262,948 B2
(45) Date of Patent: Sep. 11, 2012

(54) INTRAOCULAR LENSES WITH COMBINATIONS OF UV ABSORBERS AND BLUE LIGHT CHROMOPHORES

(75) Inventors: Walter R. Laredo, Fort Worth, TX (US); Ali E. Akinay, Mansfield, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/095,031

(22) Filed: Apr. 27, 2011

(65) Prior Publication Data

US 2011/0266505 A1 Nov. 3, 2011

Related U.S. Application Data (60) Provisional application No. 61/329,218, filed on Apr. 29, 2010.

(51) Int. Cl.
*G02B 5/23* (2006.01)
*G02C 7/02* (2006.01)
*A61K 31/74* (2006.01)
*C07D 249/04* (2006.01)
*C07D 249/16* (2006.01)
*C07D 403/00* (2006.01)
*C09K 3/00* (2006.01)

(52) U.S. Cl. .............. 252/586; 252/183.11; 351/159; 424/78.04; 514/912; 523/107; 548/255; 548/257; 548/259; 548/260; 548/261; 623/6.11

(58) Field of Classification Search .............. 252/586, 252/183.11; 523/105, 106, 107; 526/320; 534/843, 852; 548/259, 261, 260, 255, 257; 623/6.11; 351/159; 424/78.04; 514/912
See application file for complete search history.

(56) References Cited

U.S. PATENT DOCUMENTS

| | | | |
|---|---|---|---|
| 4,716,234 A | 12/1987 | Dunks et al. | |
| 5,470,932 A | 11/1995 | Jinkerson | |
| 5,543,504 A | 8/1996 | Jinkerson | |
| 5,637,726 A | 6/1997 | Collins et al. | |
| 5,693,095 A | 12/1997 | Freeman et al. | |
| 6,277,940 B1 | 8/2001 | Niwa et al. | |
| 6,528,602 B1 | 3/2003 | Freeman et al. | |
| 6,806,337 B2 | 10/2004 | Schlueter et al. | |
| 6,846,897 B2 | 1/2005 | Salamone et al. | |
| 6,872,793 B1 | 3/2005 | Schlueter | |
| 7,037,954 B2 | 5/2006 | Baba et al. | |
| 7,067,602 B2 | 6/2006 | Benz et al. | |
| 7,101,949 B2 | 9/2006 | Salamone et al. | |
| 8,043,607 B2 * | 10/2011 | Jinkerson | 424/78.04 |
| 2005/0243272 A1 | 11/2005 | Mainster et al. | |
| 2008/0090937 A1 | 4/2008 | Jinkerson et al. | |
| 2010/0012889 A1 | 1/2010 | Jinkerson | |
| 2010/0113641 A1 * | 5/2010 | Laredo | 523/107 |
| 2011/0003910 A1 | 1/2011 | Laredo | |
| 2011/0004301 A1 * | 1/2011 | Laredo | 623/6.11 |
| 2011/0178202 A1 | 7/2011 | Laredo | |

FOREIGN PATENT DOCUMENTS

| | | |
|---|---|---|
| WO | 2009/102454 | 8/2009 |
| WO | 2010/053917 | 5/2010 |
| WO | 2011/005711 | 1/2011 |
| WO | 2011005713 | 1/2011 |

OTHER PUBLICATIONS

PCT International Search Report for corresponding PCT/2011/034044 with mailing date Jul. 8, 2011.
PCT International Written Opinion for corresponding PCT/2011/034044 with mailing date Jul. 8, 2011.

* cited by examiner

*Primary Examiner* — Bijan Ahvazi
(74) *Attorney, Agent, or Firm* — Scott A. Chapple (57) ABSTRACT

Disclosed are ophthalmic device materials having improved light transmission characteristics. The materials contain a combination of certain UV absorbers and blue-light absorbing chromophores.

19 Claims, 4 Drawing Sheets

INTRAOCULAR LENSES WITH COMBINATIONS OF UV ABSORBERS AND BLUE LIGHT CHROMOPHORES

CROSS REFERENCE TO RELATED APPLICATION

This application claims priority under 35 U.S.C. §119 to U.S. Provisional Patent Application Ser. No. 61/329,218, filed Apr. 29, 2010, the entire contents of which are incorporated herein by reference.

FIELD OF THE INVENTION

This invention is directed to improved ophthalmic device materials. In particular, this invention relates to implantable ophthalmic lenses that have particular combinations of UV absorbers and blue light chromophores for providing desirable light transmission characteristics.

BACKGROUND OF THE INVENTION

In the past, benzotriazole UV absorbers, like oMTP (compound 1), have been added to intraocular lens (IOL) materials and other ophthalmic device material to provide protection from UV radiation in the environment. Typically, UV absorbers possess a polymerizable moiety, such as vinyl, acrylate or methacrylate functionality in their chemical structure, for covalent incorporation into the IOL material during polymerization. Most of these benzotriazole UV absorbers will provide a UV transmission cut-off of between 1 and 10% in the 390-410 nm range depending on concentration.

Compound 1

More recently, blue light chromophores, particularly polymerizable yellow dyes, have also been added to IOLs to absorb harmful blue light radiation. See, for example, U.S. Pat. Nos. 5,470,932 and 5,543,504. Most yellow dyes absorb blue light over a wide wavelength range and bring about a gradual attenuation of blue light, usually from 500 to 400 nm depending on the concentration of yellow dye used. If a sharper cut-off of the transmission spectrum in the blue-violet region is desired, conventional yellow dyes could not provide a sharp cut-off in that region. See, also, US 2005/0243272, which discloses ophthalmic devices having a highly selective violet light transmissive filter that selectively filters wavelengths between approximately 400 nm to about 450 nm with little or no absorption of wavelengths above 450 nm.

Even more recently, U.S. Patent Application Publication No. 2008/0090937, which is fully incorporated herein by reference for all purposes, disclosed ophthalmic materials having combinations of UV/vis absorbers and yellow dyes that provide particularly desirable blue-violet light transmission cut-offs and desirable blue light transmission cut-offs and characteristics. While materials having these transmission cut-offs and characteristic provide particular advantages over many prior art materials, these materials have limitations. As such, it would be particularly desirable to provide ophthalmic device materials with even greater ability and flexibility in providing various different transmission characteristics for ophthalmic device materials, particularly IOLs.

SUMMARY OF THE INVENTION

Ophthalmic device materials particularly suited for use as IOLs, but which are also useful for other ophthalmic devices, such as contact lenses, keratoprostheses, or corneal rings or inlays, have been discovered. These materials comprise a combination of certain UV absorbers and blue light chromophores (e.g., polymerizable yellow dyes). The materials can be tailored to have improved light transmission characteristics compared to the natural human crystalline lens, particularly in the short wavelength blue light region.

The ophthalmic device materials include:
a) a UV/vis absorber of Formula A or Formula B shown below:

Formula A wherein:
$R^1$=H, $CH_3$, $CH_2CH_3$, or $CH_2OH$;
$R^2$=$C_1$-$C_4$ alkyl or $C_1$-$C_4$ alkoxy; and
$R^3$=H, $CH_3$, $CH_3O$, F, Cl, Br, I, or $CF_3$;

Formula B wherein:
X=$C_3$-$C_4$ alkenyl, $C_3$-$C_4$ alkyl, $CH_2CH_2CH_2SCH_2CH_2$ or $CH_2CH_2CH_2SCH_2CH_2CH_2$;
Y=nothing if X=$C_3$-$C_4$ alkenyl, otherwise Y=—O—C(=O)—C($R^1$)=$CH_2$, —O—C(=O)NHCH$_2$CH$_2$OC(=O)—C($R^1$)=$CH_2$, or —O—C(=O)NHC(CH$_3$)$_2$(C$_6$H$_4$)C(CH$_3$)=$CH_2$;
$R^1$=H, $CH_3$, $CH_2CH_3$, or $CH_2OH$;
$R^2$=$C_1$-$C_4$ alkyl; and
$R^3$=H, $CH_3$, $CH_3O$, F, Cl, Br, I, or $CF_3$; and
b) a blue light chromophore that is preferably a yellow polymerizable dye.

Examples of preferred blue light chromophores are shown in Formula I and Formula II below:

Formula 1 wherein:

R¹=C(O)CH=CH₂, C(O)C(CH₃)=CH₂, C(O)NHCH₂CH₂OC(O)C(CH₃)=CH₂, or C(O)NHC(CH₃)₂C₆H₄C(CH₃)=CH₂;

R²=H, $C_1$-$C_4$ alkyl, or $C_1$-$C_4$ alkoxy;

R³=H, $C_1$-$C_4$ alkyl, F, Cl, Br, CN, NO₂, COOR⁴; XOC(O)CH=CH₂, XOC(O)C(CH₃)=CH₂, XOC(O)NHCH₂CH₂OC(O)C(CH₃)=CH₂, or XOC(O)NHC(CH₃)₂C₆H₄C(CH₃)=CH₂;

R⁴=H or $C_1$-$C_4$ alkyl; and

X=$C_1$-$C_4$ alkyl or $C_2$-$C_4$ alkenyl;

Formula II wherein:

X₁, X₂, and X₃ independently=H, $C_1$-$C_6$ alkyl, $C_1$-$C_6$ alkoxy, phenoxy, or benzyloxy;

Y=H, F, Cl, Br, I, or $C_1$-$C_6$ alkyl;

W=nothing or —O—C(=O)—NH—CH₂—CH₂—; and

Z=H, CH₃, C₂H₅, or CH₂OH.

DETAILED DESCRIPTION OF THE INVENTION

The present invention is predicated upon the use of one or more unique UV light absorbers in combination with one or more unique blue light chromophores in an ophthalmic implant device material to a achieve desired light transmission curves and/or desired blue-violet light cut-offs. These combinations of UV light absorbers and blue light chromophores allow an ophthalmic device material designer, to provide any of a wide range of different light transmission cut-off curves and/or characteristics to the implant device material depending upon the relative amounts of UV light absorber[s] and blue light chromophore[s] that are used.

Unless indicated otherwise, all component amounts are presented on a % (w/w) basis ("wt. %").

The UV absorbers of the present invention can provide a sharp transmission cut-off (i.e., less than 1% transmission) at wavelengths less than 400 nm for ophthalmic device materials, depending on UV absorber concentration. However, it is preferable that the UV absorbers of the present invention, depending upon their concentration within the ophthalmic device material, provide a sharp transmission cut-off in the short wavelength visible (405-440 nm) region of the spectrum and also provide protection from UV radiation (<400 nm). Thus, the UV absorbers can absorb both UV radiation as well as some of the shorter wavelength visible light. In one embodiment the sharp cut-off of the UV/vis absorber is at a wavelength between 410 and 440 nm, more preferably at a wavelength between 415 and 440 and even possibly at a wavelength between 425 and 431. As used herein, the term UV absorbers includes UV/vis absorbers, however, UV/vis absorbers are only those absorbers that absorb UV radiation as well as at least some visible light.

A first set of particularly desirable UV/vis absorbers for the present invention are represented formula A below:

Formula A wherein:

R¹=H, CH₃, CH₂CH₃, or CH₂OH;

R²=$C_1$-$C_4$ alkyl or $C_1$-$C_4$ alkoxy; and

R³=H, CH₃, CH₃O, F, Cl, Br, I, or CF₃.

Preferred UV/vis absorbers of Formula A of the present invention are those wherein:

R¹=H or CH₃; R²=$C_1$-$C_4$ alkoxy; and R³=H, CH₃, CH₃O, F, Cl, or CF₃.

More preferred absorbers of Formula A of the present invention are selected from the group consisting of:

2-hydroxy-5-methoxy-3-(5-(trifluoromethyl)-2H-benzo[d][1,2,3]triazol-2-yl)benzyl methacrylate;

3-(5-fluoro-2H-benzo[d][1,2,3]triazol-2-yl)-2-hydroxy-5-methoxybenzyl methacrylate;

3-(2H-benzo[d][1,2,3]triazol-2-yl)-2-hydroxy-5-methoxybenzyl methacrylate;

3-(5-chloro-2H-benzo[d][1,2,3]triazol-2-yl)-2-hydroxy-5-methoxybenzyl methacrylate;

2-hydroxy-5-methoxy-3-(5-methoxy-2H-benzo[d][1,2,3]triazol-2-yl)benzyl methacrylate;

2-hydroxy-5-methoxy-3-(5-methyl-2H-benzo[d][1,2,3]triazol-2-yl)benzyl methacrylate; and

2-hydroxy-5-methyl-3-(5-(trifluoromethyl)-2H-benzo[d][1,2,3]triazol-2-yl)benzyl methacrylate.

Most preferred UV/Vis absorbers of formula A of the present invention are 2-hydroxy-5-methoxy-3-(5-(trifluoromethyl)-2H-benzo[d][1,2,3]triazol-2-yl)benzyl methacrylate and 3-(5-chloro-2H-benzo[d][1,2,3]triazol-2-yl)-2-hydroxy-5-methoxybenzyl methacrylate.

The synthesis of the U/Vis absorbers of formula A of the present invention is described below.

Step 1: Phenol derivative 1 is synthesized via the hydroxymethylation of α-methoxyphenol as shown below.

Step 1

1

In steps 2 and 3, the diazonium salt of a 2-nitroaniline derivative is synthesized and subsequently reacted with 1 to form an azo dye.

In step 4, the azo dye is treated with a reducing agent, such as formamidinesulfinic acid, to form the corresponding benzotriazole compound. The purity of the isolated benzotriazole compound can be enhanced by techniques known in the art, including filtration of excess reducing agent and reducing agent byproducts before addition of protic acids and column chromatography.

In step 5, the benzotriazole from step 4 is esterified to form a "reactive" compound which contains a vinyl group. By "reactive" it is understood that the vinyl group can polymerize to form covalent bonds when reacted with vinyl monomers, co-monomers, macromers, crosslinking agents, and other components typically used in making polymer-based ocular materials, particularly acrylics. The reactive groups are preferably acrylate or methacrylate groups.

A second set of particularly desirable UV/vis absorbers for the present invention are represented by formula B below:

Formula B wherein:
X=$C_3$-$C_4$ alkenyl, $C_3$-$C_4$ alkyl, $CH_2CH_2CH_2SCH_2CH_2$ or $CH_2CH_2CH_2SCH_2CH_2CH_2$;

Y=nothing if X=$C_3$-$C_4$ alkenyl, otherwise
Y=—O—C(=O)—C($R^1$)=$CH_2$, —O—C(=O)NHCH_2CH_2OC(=O)—C($R^1$)=$CH_2$, or
—O—C(=O)NHC($CH_3$)_2($C_6H_4$)C($CH_3$)=$CH_2$;
$R^1$=H, $CH_3$, $CH_2CH_3$, or $CH_2OH$;
$R^2$=$C_1$-$C_4$ alkyl; and
$R^3$=H, $CH_3$, $CH_3O$, F, Cl, Br, I, or $CF_3$.

Preferably, the UV/Vis absorbers of Formula B of the present invention are those wherein:

X=$C_3$-$C_4$ alkenyl, $C_3$-$C_4$ alkyl, or $CH_2CH_2CH_2SCH_2CH_2$;

Y=nothing if X=$C_3$-$C_4$ alkenyl, otherwise Y=—O—C(=O)—C($R^1$)=$CH_2$;

$R^1$=H or $CH_3$;

$R^2$=$C_1$-$C_2$ alkyl, and $R^3$=$CH_3$, $CH_3O$, F, Cl, or $CF_3$.

Three preferred absorbers of formula B of the present invention are:

2-(3-(3-(5-chloro-2H-benzo[d][1,2,3]triazol-2-yl)-4-hydroxy-5-methoxy-phenyl)propylthio)ethyl methacrylate ("Compound 1");

4-allyl-2-(5-chloro-2H-benzo[d][1,2,3]triazol-2-yl)-6-methoxyphenol ("Compound 2"),

3-(3-(5-chloro-2H-benzo[d][1,2,3]triazol-2-yl)-4-hydroxy-5-methoxy-phenyl)propyl methacrylate ("Compound 3");

4-allyl-2-methoxy-6-(5-(trifluoromethyl)-2H-benzo[d][1,2,3]triazol-2-yl)phenol ("Compound 4"); and

3-(4-hydroxy-3-methoxy-5-(5-(trifluoromethyl)-2H-benzo[d][1,2,3]triazol-2-yl)phenyl)propyl methacrylate ("Compound 5").

Compound 1

Compound 2

Compound 3

Compound 4

Compound 5

The synthesis of the UV/Vis absorbers of Formula B of the present invention is described below.

1. The UV absorbers are synthesized in 4-6 steps. In Step 1, the phenol derivative 1 is synthesized via the hydroxymethylation of eugenol, an inexpensive starting material derived from essential oils such as clove oil, nutmeg, cinnamon, and bay leaf.

Step 1

2. In steps 2 and 3, the diazonium salt of a 2-nitroaniline derivative is prepared and subsequently reacted with 1 to form an azo dye.

3. In step 4, the azo dye is treated with a reducing agent, such as formamidinesulfinic acid, to form the corresponding benzotriazole compound. At this stage, the benzotriazole can be incorporated in IOL formulations due the presence of the propenyl double bond, which can polymerize under free radical conditions. Alternatively, the double bond can be converted to other more preferable functional groups as shown in steps 5 and 6.

Step 4

Azo dye

Compound 2
Benzotriazole

4. The benzotriazole from step 4 can be further reacted as shown in steps 5 and 6 to form an intermediate that contains hydroxyl groups which can then be esterified to contain (meth)acrylate groups. The incorporation of hydroxyl groups can be carried out using a wide range of synthetic methodologies, including Michael Addition using mercaptans or hydroboration/oxidation using boron containing compounds such as borane-methyl sulfide complexes. The resulting hydroxyl groups can then be converted to polymerizable (meth)acrylate groups. The (meth)acrylate groups can then form covalent bonds when reacted with vinyl monomers, co-monomers, macromers, crosslinking agents, and other components typically used in making polymer-based ocular materials, particularly acrylics.

The UV/Vis absorbers of the present invention are suitable for use in ophthalmic device material, particularly IOLs. IOL materials will generally contain from 0.1 to 5% (w/w) of a UV/Vis absorber of the present invention. Preferably, IOL materials will contain from 0.5 to 4% (w/w) of an absorber of the present invention. Most preferably, IOL materials will contain from 1 to 3% (w/w) of an absorber of the present invention. Such device materials are prepared by copolymerizing the absorbers of the present invention with other ingredients, such as device-forming materials and cross-linking agents.

One particular advantage of the UV/vis absorbers of the present invention is that relatively low concentrations of the absorbers within the device materials, particularly when used in IOLs, can provide desirable UV/vis cutoffs in the 405 to 440 nm wavelength range. It is preferable for the UV/vis absorbers to exhibit less than 10% transmission of light at a wavelength of 440 nm using a concentration of UV/vis absorbers that is no greater than 4.0%, more preferably no greater than 3.6% and even more preferably no greater than 3.33% of the device material. It is also preferable for the UV/vis absorbers to exhibit no greater than 1% transmission of light at a wavelength of 430 nm using a concentration of UV/vis absorbers that is no greater than 4.0%, more preferably no greater than 3.3% and even more preferably no greater than 3.0% of the device material. It is also preferable for the UV/vis absorbers to exhibit no greater than 10% transmission of light at a wavelength of 420 nm using a concentration of UV/vis absorbers that is no greater than 0.80%, more preferably no greater than 0.60% and even more preferably no greater than 0.45% of the device material. It is also preferable for the UV/vis absorbers to exhibit no greater

Steps 5 and 6 than 1% transmission of light at a wavelength of 410 nm using a concentration of UV/vis absorbers that is no greater than 0.65%, more preferably no greater than 0.50% and even more preferably no greater than 0.44% of the device material. It should be noted that the low light transmission values listed in this paragraph are achieved substantially solely by the UV/vis absorber in the absence of any other material or compound that provides or enhances these values to any substantial extent. Thus is can be said that the UV/vis absorber provides at least 90%, more preferably at least 96% and even more preferably at least 99% of the light blocking and/or absorption necessary to achieve these values. Moreover, these values can be measured in accordance with the protocol provided in Example 1 as modified for any particular device material.

The blue light chromophores of the present invention are preferably azo compounds. A first set of desirable azo compounds of the present invention have the following structure:

Formula I wherein:
R$^1$=C(O)CH=CH$_2$, C(O)C(CH$_3$)=CH$_2$, C(O)NHCH$_2$CH$_2$OC(O)C(CH$_3$)=CH$_2$, or C(O)NHC(CH$_3$)$_2$C$_6$H$_4$C(CH$_3$)=CH$_2$;
R$^2$=H, C$_1$-C$_4$ alkyl, or C$_1$-C$_4$ alkoxy;
R$^3$=H, C$_1$-C$_4$ alkyl, F, Cl, Br, CN, NO$_2$, COOR$^4$; XOC(O)CH=CH$_2$, XOC(O)C(CH$_3$)=CH$_2$, XOC(O)NHCH$_2$CH$_2$OC(O)C(CH$_3$)=CH$_2$, or XOC(O)NHC(CH$_3$)$_2$C$_6$H$_4$C(CH$_3$)=CH$_2$;
R$^4$=H or C$_1$-C$_4$ alkyl; and
X=C$_1$-C$_4$ alkyl or C$_2$-C$_4$ alkenyl.

Preferred compounds of Formula I are those wherein:
R$^1$=C(O)CH=CH$_2$, C(O)C(CH$_3$)=CH$_2$, or C(O)NHCH$_2$CH$_2$OC(O)C(CH$_3$)=CH$_2$;
R$^2$=H or C$_1$-C$_4$ alkyl;
R$^3$=H, C$_1$-C$_4$ alkyl, F, Cl, Br, CN, NO$_2$, COOR$^4$; XOC(O)CH=CH$_2$, XOC(O)C(CH$_3$)=CH$_2$, or XOC(O)NHCH$_2$CH$_2$OC(O)C(CH$_3$)=CH$_2$;
R$^4$=C$_1$-C$_4$ alkyl; and
X=C$_1$-C$_4$ alkyl.

Most preferred compounds of Formula I are those wherein:
R$^1$=C(O)C(CH$_3$)=CH$_2$ or C(O)NHCH$_2$CH$_2$OC(O)C(CH$_3$)=CH$_2$;
R$^2$=H;
R$^3$=H, C$_1$-C$_4$ alkyl, F, Cl, Br, XOC(O)C(CH$_3$)=CH$_2$ or XOC(O)NHCH$_2$CH$_2$OC(O)C(CH$_3$)=CH$_2$; and
X=C$_1$-C$_4$ alkyl.

Especially preferred compounds of Formula I are (E)-4-((2-hydroxy-5-methylphenyl)diazenyl)phenethyl methacrylate ("Compound A") and (E)-4-hydroxy-3-((4-(2-(methacryloyloxy)ethyl)phenyl)diazenyl)phenethyl methacrylate ("Compound B").

Compound A

Chemical Formula: C$_{19}$H$_{20}$N$_2$O$_3$
Molecular Weight: 324.37

Compound B

Chemical Formula: C$_{24}$H$_{26}$N$_2$O$_5$
Molecular Weight: 422.47

A representative synthesis of the azo compounds of Formula I is as follows. The compounds of Formula I are synthesized in 2-3 steps.

1. In steps 1-2, the diazonium salt of an aniline derivative is prepared and subsequently reacted with a desired phenol compound to form an azo dye.

Azo dyes

2. In step 3, the free primary alcohol groups of the azo dyes are esterified to form a polymerizable azo dye containing at least one (meth)acrylate group. The (meth)acrylate group can then form covalent bonds when reacted with vinyl monomers, co-monomers, macromers, crosslinking agents, and other components typically used in the manufacturing of IOLs.

3.

Polymerizable Azo Dyes

The azo compounds of Formula I of the present invention are suitable for use in ophthalmic device materials, particularly IOLs. IOL materials will generally contain from 0.005 to 0.2% (w/w) of a compound of Formula I. Preferably, IOL materials will contain from 0.01 to 0.1% (w/w) of a compound of Formula I of the present invention. Most preferably, IOL materials will contain from 0.01 to 0.05% (w/w) of a compound of Formula I of the present invention. Such device materials are prepared by copolymerizing the compounds of Formula I with other ingredients, such as device-forming materials and cross-linking agents. The IOL or other ophthalmic device materials containing the compounds of Formula I optionally contain UV absorbers and other visible light absorbers.

A second set of desirable azo compounds of the present invention have the following structure:

Formula II wherein:

$X_1$, $X_2$, and $X_3$ independently=H, $C_1$-$C_6$ alkyl, $C_1$-$C_6$ alkoxy, phenoxy, or benzyloxy;

Y=H, F, Cl, Br, I, or $C_1$-$C_6$ alkyl;

W=nothing or —O—C(=O)—NH—$CH_2$—$CH_2$—; and

Z=H, $CH_3$, $C_2H_5$, or $CH_2OH$.

Preferred compounds of Formula II are those wherein:

$X_1$, $X_2$, and $X_3$ independently=H, $C_1$-$C_4$ alkyl, or $C_1$-$C_4$ alkoxy, Y=H, Cl or $C_1$-$C_4$ alkyl;

W=nothing; and

Z is H or $CH_3$.

More preferred compounds of Formula II are the following three compounds: 2-hydroxy-3-((4-methoxyphenyl)diazenyl)-5-methylbenzyl methacrylate ("Compound A"); 2-hydroxy-5-methyl-3-((3,4,5-trimethoxy-phenyl)diazenyl)benzyl methacrylate ("Compound B"); and 5-chloro-2-hydroxy-3-((4-methoxyphenyl)diazenyl)benzyl methacrylate ("Compound C").

Compound A

Compound B

Compound C

Most preferred compounds of Formula II are Compounds A and B.

A representative synthesis of the azo compounds of Formula II is as follows.

1. In Steps 1-2, the diazonium salt of a 2-nitroaniline derivative is prepared and subsequently reacted with a desired phenol compound to form an azo dye.

2. In step 3, the free hydroxyl group of the azo dye is esterified to form a polymerizable azo dye containing a (meth)acrylate group. The (meth)acrylate group can then form covalent bonds when reacted with vinyl monomers, co-monomers, macromers, crosslinking agents, and other components typically used in making copolymeric ocular materials, particularly acrylic IOLs.

Polymerizable Azo Dye

The azo compounds of formula II the present invention are suitable for use in ophthalmic device materials, particularly IOLs. IOL materials will generally contain from 0.005 to 0.2% (w/w) of a compound of Formula II. Preferably, IOL materials will contain from 0.01 to 0.08% (w/w) of a compound of the present invention. Most preferably, IOL materials will contain from 0.01 to 0.05% (w/w) of a compound of the present invention. Such device materials are prepared by copolymerizing the compounds of Formula II with other ingredients, such as device-forming materials and cross-linking agents. The IOL or other ophthalmic device materials containing the compounds of Formula II optionally contain UV absorbers and other visible light absorbers.

The UV/vis absorbers and blue light chromophores disclosed above are also disclosed in the following U.S. patent applications: application Ser. No. 12/611539, filed Nov. 3, 2009; Application Ser. No. 61/223,275 filed Jul. 6, 2009; Application Ser. No. 61/223,251 filed Jul. 6, 2009; and Application Ser. No. 61/295,900, all of which are fully incorporated herein by reference for all purposes.

It is additionally contemplated that, depending upon the results to be achieved, other blue light chromophores may be employed in the present invention as well. For example, and without limitation, U.S. Patent Application Publication No. 2008/0090937, which is fully incorporated herein by reference for all purposes, discloses yellow dyes that can be employed in embodiments of the present invention.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula III:

wherein for formula IV:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_nH_{2n'+1}$ (n'=1-10), iso-$OC_3H_7$, $C_6H_5$, or $CH_2C_6H_5$;
w is 0-6, provided that m+w$\leq$8; and
D is H, $C_1$-$C_4$ alkyl, $C_1$-$C_4$ alkoxy, $C_6H_5$, $CH_2C_6H_5$ or halogen.

Preferred monomers of formula III are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula III are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to an absorber of the present invention and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—($CH_2CH_2$O$)_p$—C(=O)C($CH_3$)=$CH_2$ where p=1-50; and $CH_2$=C($CH_3$)C(=O)O($CH_2)_tO$—C(=O)C($CH_3$)=$CH_2$ where t=3-20; and their corresponding acrylates. A preferred cross-linking monomer is $CH_2$=$C(CH_3)C$(=O)O—($CH_2CH_2O)_p$—C(=O)C($CH_3$)=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds with molecular weights typically between 500-5000 Daltons.

Suitable polymerization initiators for device materials containing a UV/Vis absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

Preferably, the ingredients and their proportion are selected so that the device materials of the present invention possess the following properties, which make the materials of the present invention particularly suitable for use in IOLs which are to be inserted through incisions of 4 mm or less. For convenience, the device materials may be referred to as lens materials.

The lens material preferably has a refractive index in the dry state of at least about 1.50 as measured by an Abbe' refractometer at 589 nm (Na light source). For a given optic diameter, optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably below about 25° C., and more preferably below about 15° C. Tg is measured by differential scanning calorimetry at 10° C./min., and is determined as the half-height of the heat capacity increase.

The lens material will have an elongation (strain at break) of at least 75%, preferably at least 90%, and most preferably at least 100%. This property indicates that the lens generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using a tensile tester. The grip distance is set at 11 mm and a crosshead speed is set at 500 mm/minute and the sample is pulled to failure. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain.

As a particular advantage of the present invention, the UV/vis absorber can be combined with the blue light chromophore to provide for a wide range of transmission or absorption of light at 450 nm. Preferably, the range is as wide as from 40% transmission (T) to 80% transmission (T), more typically from 25% T to 90% T and even possibly from 15% T to 99% T. This wide range provides an ophthalmic device material designer with a great deal of flexibility in tailoring the desired transmission for a particular individual or group of individuals or tailoring the desired transmission for particular environmental conditions.

It will be understood that any one or more of the UV absorbers of the present invention can be combined with any one or more of the blue light chromophores of the present invention in an ophthalmic implant device material of the present invention. Moreover, various different concentrations of the UV absorber[s] and the blue light chromophore[s] can be used as well. However, some particular combinations of UV absorber[s] and blue light chromophore[s] as well as particular concentrations of the UV absorber[s] and the blue light chromophore[s] are believed to be particularly desirable.

The invention will be further illustrated by the following examples, which are intended to be illustrative, but not limiting.

Example 1

A monomer diluent formulation consisting of 2-phenylethyl acrylate (PEA), hydroxyethyl methacrylate (HEMA), and 1,4-butanediol diacrylate (BDDA) was prepared by mixing the three monomers together in the proportions of 80:15:3.2 parts by weight. Then UV absorber of the following formula:

(WL-1)

AL59520
2-hydroxy-5-methoxy-3-(5-(trifluoromethyl)-2H-benzo[d][1,2,3]triazol-2-yl)benzyl methacrylate and blue light chromophore in the form of yellow dye according to the following formula:

"WL-A"

Figure 1:
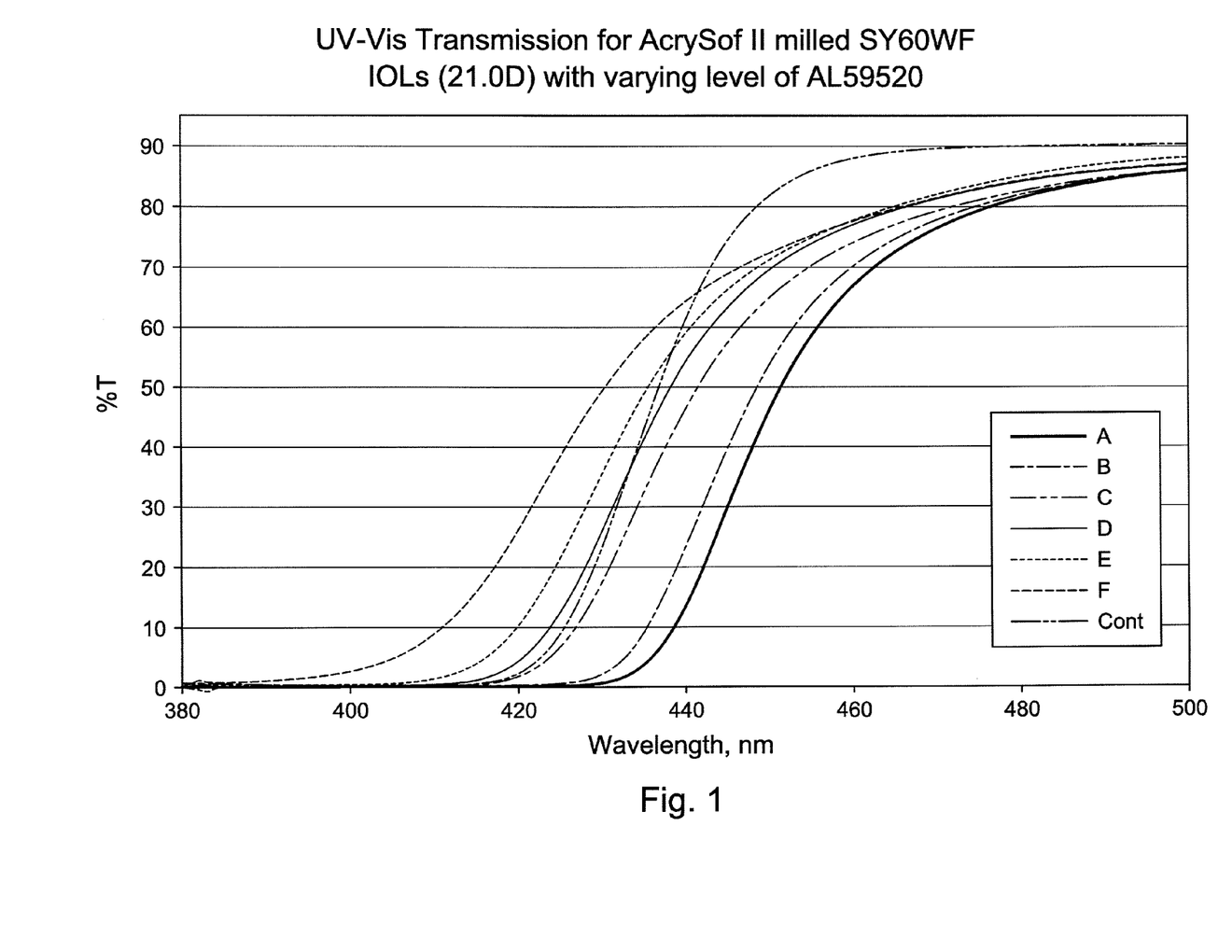
FIGS. 1 through 4 show the transmittance of the ophthalmic device materials and solution of Examples 1 and 2.

2-hydroxy-3-((4-methoxyphenyl)diazenyl)-5-methylbenzyl methacrylate were added to 3 g of the diluent formulation as reported in Table 1 below. Each formulation was initiated with 1.8% Perkadox 16S and cured in 21.0D SN60WF lens molds at 105° C. for 3 h. The lenses were demolded, placed into stainless steel extraction trays, extracted with acetone, and vacuum dried to remove residual acetone. After extraction and vacuum drying, samples were analyzed by UV-Visible transmission spectroscopy from 300-800 nm using a Perkin-Elmer Lambda 35 instrument equipped with a Lab Sphere RSA-PE-20 integrating sphere. FIG. 1 shows transmission curves obtained from these lenses and Table 1 summarizes the transmission characteristics of the formulations.

"WL-E"

2-hydroxy-5-methyl-3-(p-tolyldiazenyl)benzyl methacrylate

TABLE 1

Formulations and UV-Vis Data for IOLs with Varying Concentrations of UV absorber

| Chromophore Conc. | WL-1 Conc. Wt % | % Transmission at: | | | | Absorbance at: | | | |
|---|---|---|---|---|---|---|---|---|---|
| | | 440 nm | 430 nm | 420 nm | 410 nm | 440 nm | 430 nm | 420 nm | 410 nm |
| 0.02 | 3.30 | 13.821 | 0.672 | 0.270 | 0.227 | 0.8595 | 2.1726 | 2.5686 | 2.6440 |
| 0.02 | 2.40 | 23.267 | 2.209 | 0.237 | 0.220 | 0.6333 | 1.6558 | 2.6253 | 2.6576 |
| 0.02 | 0.82 | 46.196 | 17.473 | 1.869 | 0.289 | 0.3354 | 0.7576 | 1.7284 | 2.5391 |
| 0.02 | 0.60 | 53.845 | 25.927 | 4.474 | 0.149 | 0.2689 | 0.5862 | 1.3493 | 2.8265 |
| 0.02 | 0.40 | 58.910 | 35.501 | 10.311 | 1.481 | 0.2298 | 0.4498 | 0.9867 | 1.8294 |
| 0.02 | 0.20 | 64.376 | 49.210 | 26.132 | 8.980 | 0.1913 | 0.3079 | 0.5828 | 1.0467 |
| 0.00 | 0.81 | 61.139 | 23.428 | 2.372 | 0.252 | 0.2137 | 0.6303 | 1.6249 | 2.5986 |

FIG. 1 shows UV-Visible transmission spectra varying U.V. absorber concentration, as follows: A=3.30%, B=2.40%, C=0.82%, D=0.60%, E=0.40%, F=0.20% and all with a blue light chromophore concentration ~0.02%, except for the control, which had 0.81% UV absorber and no blue light chromophore.

Example 2

In example 2, solutions were formed that included combinations of UV absorbers and blue light chromophores according in concentrations that would be suitable for the device material of the present invention. In particular, twenty toluene solutions were prepared. Each of the twenty solutions contained 0.2 or 2% of the UV absorber of example 1 (i.e., "WL-1"). Six of the twenty solutions contained 0.01 or 0.04% of the blue light chromophore of example 1(i.e., "WL-A"). Six of the solutions contained 0.01 or 0.04% of the blue light chromophore below:

Another six of the twenty solutions contained 0.01 or 0.04% of the blue light chromophore below:

"WL-F"

4-((2-hydroxy-5-methylphenyl)diazenyl)phenethyl methacrylate

Figure 2:
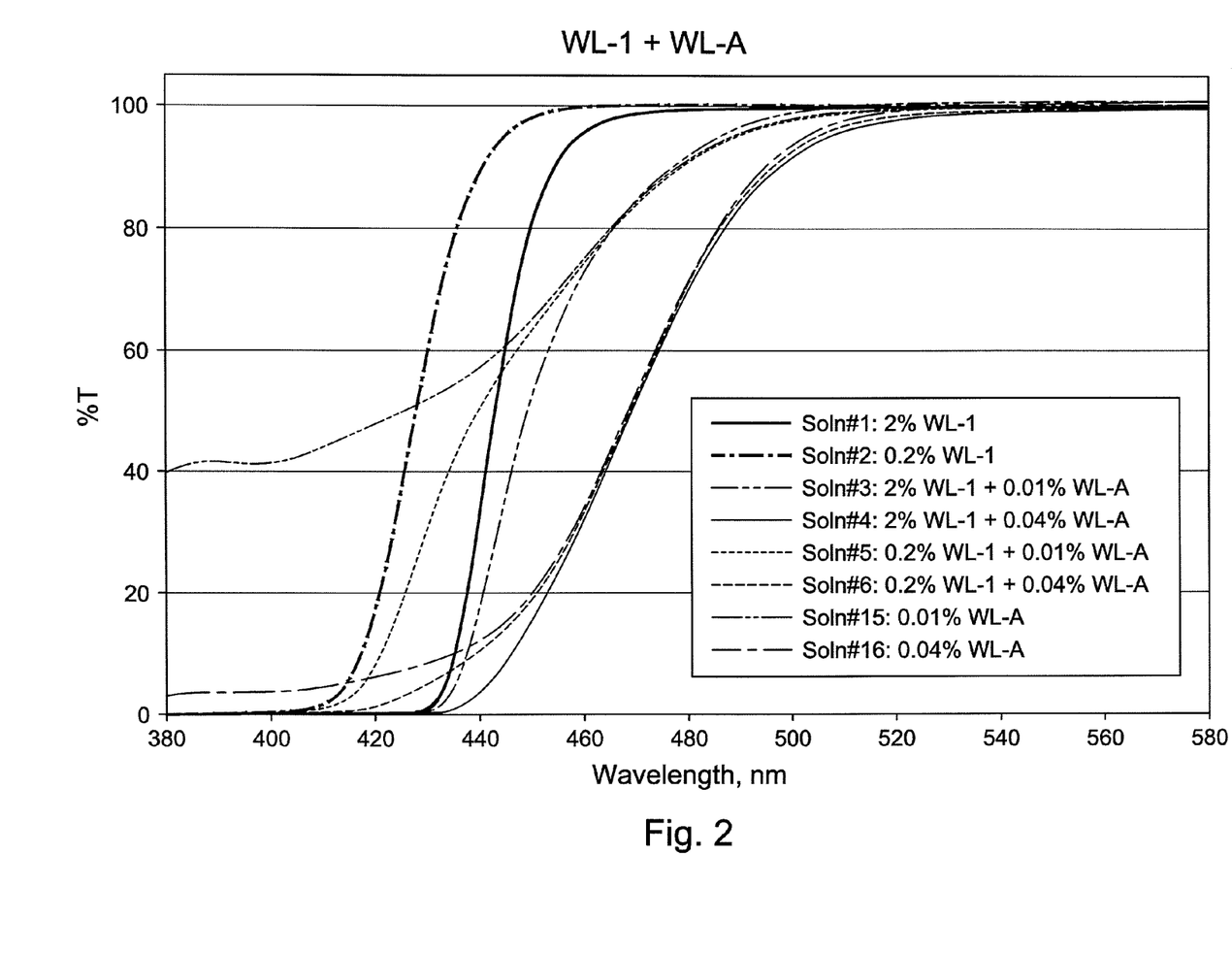
Figure 3:
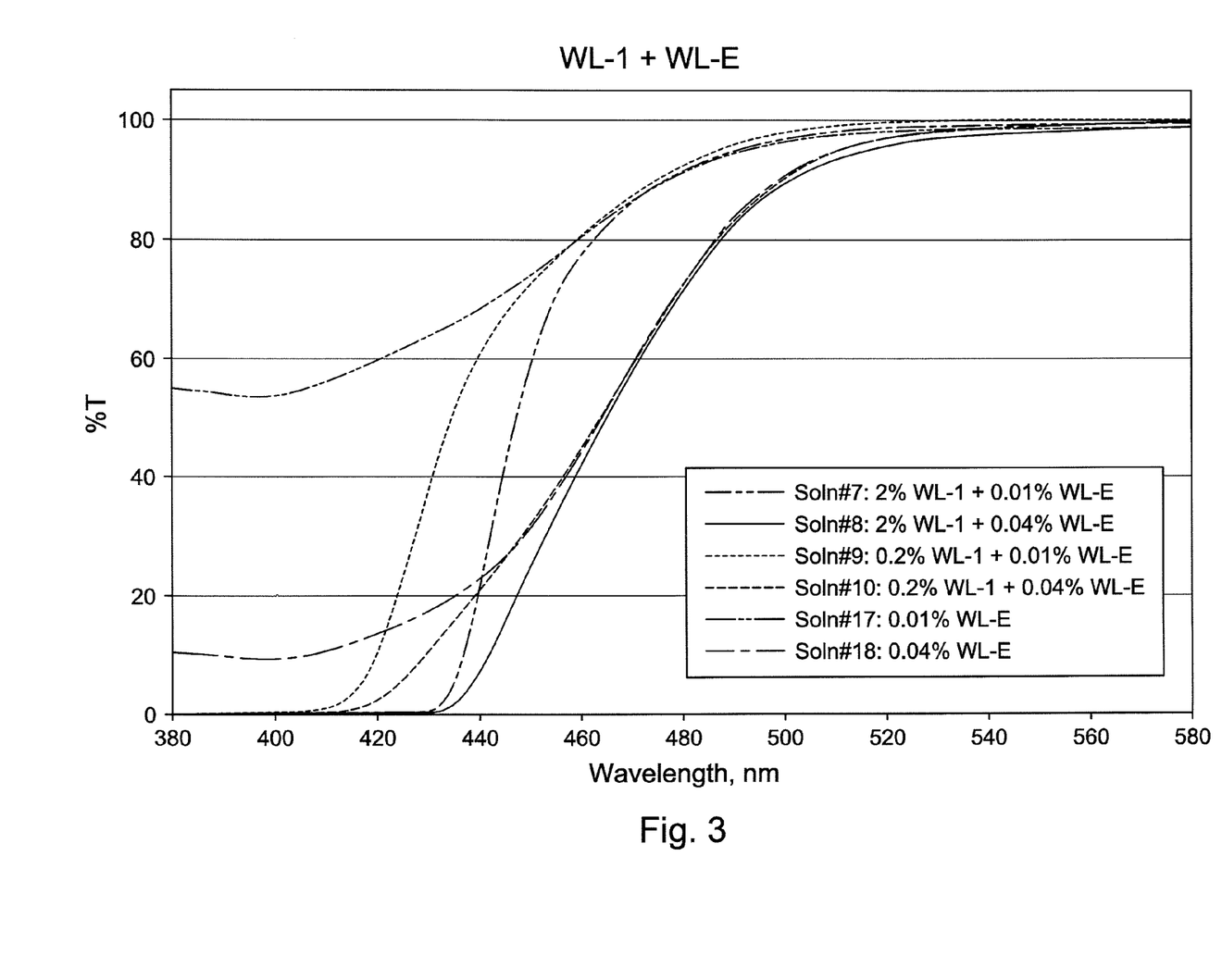
Figure 4:
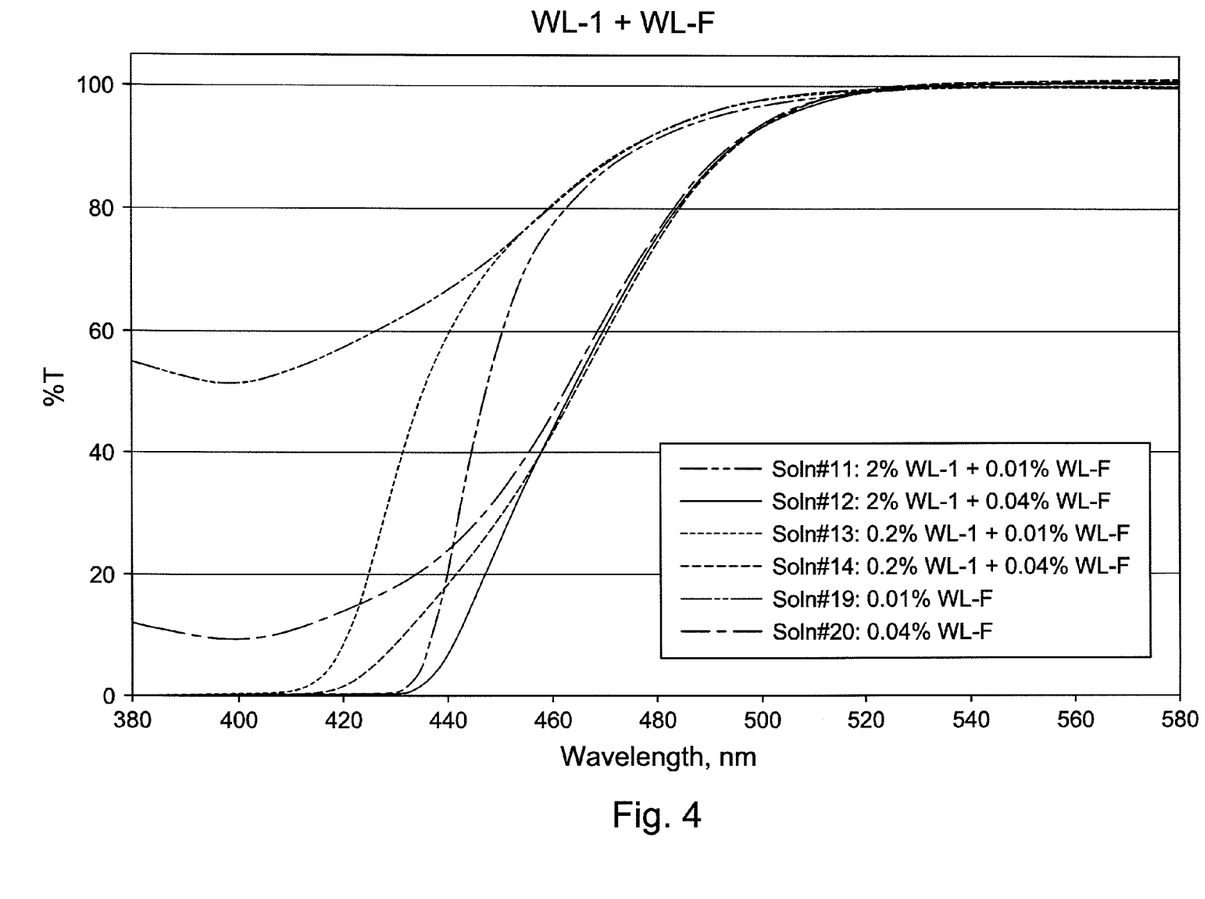

The concentrations and transmission data are provided in Table 2. The transmission spectra of corresponding solutions are shown in FIGS. 2, 3 and 4, respectively.

TABLE 2

| Solution No. | Absorber Conc. Wt % | | Wavelength @ 1% T | Wavelength @ 10% T | Wavelength @ 50% T | % T @ 450 nm | % T @ 500 nm |
|---|---|---|---|---|---|---|---|
| | | WL-A Conc. Wt % | | | | | |
| 1 | 2 | 0 | 430 | 435 | 443 | 81 | 99 |
| 2 | 0.2 | 0 | 408 | 417 | 428 | 98 | 99 |
| 3 | 2 | 0.01 | 432 | 438 | 449 | 52 | 99 |
| 4 | 2 | 0.04 | 435 | 446 | 469 | 15 | 92 |
| 5 | 0.2 | 0.01 | 411 | 421 | 440 | 63 | 98 |
| 6 | 0.2 | 0.04 | 419 | 439 | 469 | 19 | 93 |
| 7 | 0 | 0.01 | — | — | 425 | 65 | 98 |
| 8 | 0 | 0.04 | 362 | 435 | 468 | 20 | 94 |

TABLE 2-continued

| Solution No. | Absorber Conc. Wt % | | Wavelength @ 1% T | Wavelength @ 10% T | Wavelength @ 50% T | % T @ 450 nm | % T @ 500 nm |
|---|---|---|---|---|---|---|---|
| | | WL-E Conc. Wt % | | | | | |
| 9 | 2 | 0.01 | 431 | 437 | 447 | 59.5 | 98 |
| 10 | 2 | 0.04 | 434 | 442 | 465 | 25 | 91 |
| 11 | 0.2 | 0.01 | 410 | 420 | 434 | 73 | 99 |
| 12 | 0.2 | 0.04 | 416 | 429 | 464 | 31 | 91 |
| 13 | 0 | 0.01 | — | — | 367 | 74 | 97 |
| 14 | 0 | 0.04 | 348 | 407 | 464 | 32 | 91 |
| | | WL-F Conc. Wt % | | | | | |
| 15 | 2 | 0.01 | 432 | 437 | 448 | 58 | 98 |
| 16 | 2 | 0.04 | 434 | 442 | 464 | 26 | 94 |
| 17 | 0.2 | 0.01 | 411 | 421 | 435 | 72 | 98 |
| 18 | 0.2 | 0.04 | 417 | 431 | 464 | 29 | 93 |
| 19 | 0 | 0.01 | — | — | 405 | 73 | 98 |
| 20 | 0 | 0.04 | — | 410 | 462 | 33 | 94 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:

1. An ophthalmic device material comprising:
a) a UV/Vis absorber of Formula A or Formula B shown below:

Formula A wherein:
$R^1$=H, $CH_3$, $CH_2CH_3$; or $CH_2OH$;
$R^2$=$C_1$-$C_4$ alkyl or $C_1$-$C_4$ alkoxy; and
$R^3$=H, $CH_3$, $CH_3O$, F, Cl, Br, I, or $CF_3$;

Formula B wherein:
X=$C_3$-$C_4$ alkenyl, $C_3$-$C_4$ alkyl, $CH_2CH_2CH_2SCH_2CH_2$ or $CH_2CH_2CH_2SCH_2CH_2CH_2$;
Y=nothing if X=$C_3$-$C_4$ alkenyl, otherwise Y=—O—C(=O)—C($R^1$)=$CH_2$, —O—C(=O)NHCH_2CH_2OC(=O)—C($R^1$)=$CH_2$, or —O—C(=O)NHC($CH_3$)_2($C_6H_4$)C($CH_3$)=$CH_2$;
$R^1$=H, $CH_3$, $CH_2CH_3$, or $CH_2OH$;
$R^2$=$C_1$-$C_4$ alkyl; and
$R^3$=H, $CH_3$, $CH_3O$, F, Cl, Br, I, or $CF_3$; and b) a blue light chromophore, wherein the blue light chromophore is of Formula I or Formula II as shown below:

Formula I wherein:
$R^1$=C(O)CH=$CH_2$, C(O)C($CH_3$)=$CH_2$, C(O)NHCH_2CH_2OC(O)C($CH_3$)=$CH_2$, or C(O)NHC($CH_3$)_2$C_6H_4$C($CH_3$)=$CH_2$;
$R^2$=H, $C_1$-$C_4$ alkyl, OR $C_1$-$C_4$ alkoxy;
$R^3$=H, $C_1$-$C_4$ alkyl, F, Cl, Br, CN, $NO_2$, COOR$^4$; XOC(O)CH=$CH_2$, XOC(O)C($CH_3$)=$CH_2$, XOC(O)NHCH_2CH_2OC(O)C($CH_3$)=$CH_2$, or XOC(O)NHC($CH_3$)_2$C_6H_4$C($CH_3$)=$CH_2$;
$R^4$=H or $C_1$-$C_4$ alkyl; and
X=$C_1$-$C_4$ alkyl or $C_2$-$C_4$ alkenyl;

Formula II wherein:
$X_1$, $X_2$, and $X_3$ independently=H, $C_1$-$C_6$ alkyl, $C_1$-$C_6$ alkoxy, phenoxy, or benzyloxy;
Y=H, F, Cl, Br, I, or $C_1$-$C_6$ alkyl;

W=direct bond or —O—C(=O)—NH—CH$_2$—CH$_2$—; and

Z=H, CH$_3$, C$_2$H$_5$, or CH$_2$OH; and c) device forming polymeric material.

2. The ophthalmics device material according to claim 1, wherein the UV/Vis absorber includes a compound of Formula A, wherein R$^1$=H or CH$_3$; R$^2$=C$_1$-C$_4$ alkoxy; and R$^3$=H, CH$_3$, CH$_3$O, F, Cl, or CF$_3$.

3. The opthalmic device material according to claim 2, wherein the compound of Formula A are selected from the group consisting of:

2-hydroxy-5-methoxy-3-(5-(trifluoromethyl)-2H-benzo[d][1,2,3]triazol-2-yl)benzyl methacrylate;

3-(5-fluoro-2H-benzo[d][1,2,3]triazol-2-yl)-2-hydroxy-5-methoxybenzyl methacrylate;

3-(2H-benzo[d][1,2,3]triazol-2-yl)-2-hydroxy-5-methoxybenzyl methacrylate;

3-(5-chloro-2H-benzo[d][1,2,3]triazol-2-yl)-2-hydroxy-5-methoxybenzyl methacrylate;

2-hydroxy-5-methoxy-3-(5-methoxy-2H-benzo[d][1,2,3]triazol-2-yl)benzyl methacrylate;

2-hydroxy-5-methoxy-3-(5-methyl-2H-benzo[d][1,2,3]triazol-2-yl)benzyl methacrylate; and 2-hydroxy-5-methyl-3-(5-(trifluoromethyl)-2H-benzo[d][1,2,3]triazol-2-yl)benzyl methacrylate.

4. The opthalmic device material according to claim 3, wherein the compound of Formula A is selected from the group consisting of 2-hydroxy-5-methoxy-3-(5-(trifluoromethyl)-2H-benzo[d][1,2,3]triazol-2-yl)benzyl methacrylate and 3-(5-chloro-2H-benzo[d][1,2,3]triazol-2-yl)-2-hydroxy-5-methoxybenzyl methacrylate.

5. The opthalmic implant device material according to claim 1, wherein the UV/Vis absorber includes a compound of Formula B wherein:

X=C$_3$-C$_4$alkenyl, C$_3$-C$_4$ alkyl, or CH$_2$CH$_2$CH$_2$SCH$_2$CH$_2$;

Y=nothing if X=C$_3$-C$_4$ alkenyl, otherwise Y=—O—C(=O)—C(R$^1$)=CH$_2$;

R$^1$=H or CH$_3$;

R$^2$=C$_1$-C$_2$ alkyl; and

R$^3$=CH$_3$, CH$_3$O, F, Cl, or CF$_3$.

6. The opthalmic device material according to claim 5, wherein the compound of Formula B is selected from the group consisting of:

2-(3-(3-(5-chloro-2H-benzo[d][1,2,3]triazol-2-yl)-4-hydroxy-5-methoxy-phenyl)propylthio)ethyl methacrylate;

4-allyl-2-(5-chloro-2H-benzo[d][1,2,3]triazol-2-yl)-6-methoxyphenol;

3-(3-(5-chloro-2H-benzo[d][1,2,3]triazol-2-yl)-4-hydroxy-5-methoxy-phenyl)propyl methacrylate ("Compound 3");

4-allyl-2-methoxy-6-(5-(trifluoromethyl)-2H-benzo[d][1,2,3]triazol-2-yl)phenol and 3-(4-hydroxy-3-methoxy-5-(5-(trifluoromethyl)-2H-benzo[d][1,2,3]triazol-2-yl)phenyl)propyl methacrylate.

7. The ophthalmic device material according to claim 1, wherein the device material contains from 0.5 to 4% w/w of the UV/Vis absorber.

8. The ophthalmic device material according to claim 1, wherein the UV/Vis absorber is copolymerized with one or more other ingredients selected from device-forming materials and cross-linking agents.

9. The ophthalmic device material according to claim 1, wherein the blue light chromophore is included in the ophthalmic device material at a concentration from 0.01 to 0.08% w/w.

10. The ophthalmic device material according to claim 1, wherein the blue light chromophore is copolymerized with one or more other ingredients selected from device-forming materials and cross-linking agents.

11. The ophthalmic device comprising the material of claim 1, wherein the ophthalmic device is selected from the group consisting of intraocular lenses; contact lenses; keratoprostheses; and corneal rings or inlays.

12. The ophthalmic device material according to claim 1 wherein the blue light chromophore includes a compound of Formula I, wherein:

R$^1$=C(O)CH=CH$_2$, C(O)C(CH$_3$)=CH$_2$, or C(O)NHCH$_2$CH$_2$OC(O)C(CH$_3$)=CH$_2$;

R$^2$=H or C$_1$-C$_4$ alkyl;

R$^3$=H, C$_1$-C$_4$ alkyl, F, Cl, Br, CN, NO$_2$, COOR$^4$; XOC(O)CH=CH$_2$, XOC(O)C(CH$_3$)=CH$_2$, or XOC(O)NHCH$_2$CH$_2$OC(O)C(CH$_3$)=CH$_2$;

R$^4$=C$_1$-C$_4$ alkyl; and

X=C$_1$-C$_4$ alkyl.

13. The ophthalmic device material according to claim 1 wherein the blue light chromophore includes a compound of Formula I, wherein:

R$^1$=C(O)C(CH$_3$)=CH$_2$ or C(O)NHCH$_2$CH$_2$OC(O)C(CH$_3$)=CH$_2$;

R$^2$=H;

R$^3$=H, C$_1$-C$_4$ alkyl, F, Cl, Br, XOC(O)C(CH$_3$)=CH$_2$ or XOC(O)NHCH$_2$CH$_2$OC(O)C(CH$_3$)=CH$_2$; and X=C$_1$-C$_4$ alkyl.

14. The ophthalmic device material according to claim 1 wherein the blue light chromophore includes a compound of Formula I selected from (E)-4-((2-hydroxy-5-methylphenyl)diazenyl)phenethyl methacrylate and (E)-4-hydroxy-3-((4-(2-(methacryloyloxy)ethyl)phenyl)diazenyl)phenethyl methacrylate.

15. The ophthalmic device material according to claim 1 wherein the blue light chromophore includes a compound of Formula II, wherein:

X$_1$, X$_2$, and X$_3$ independently=H, C$_1$-C$_4$ alkyl, or C$_1$-C$_4$ alkoxy, Y=H, C$_1$ or C$_1$-C$_4$ alkyl;

W=direct bond; and

Z is H or CH$_3$.

16. The ophthalmic device material according to claim 1 the blue light chromophore includes a compound of Formula II selected from 2-hydroxy-3-((4-methoxyphenyl)diazenyl)-5-methylbenzyl methacrylate; 2-hydroxy-5-methyl-3-((3,4,5-trimethoxy-phenyl)diazenyl)benzyl methacrylate; and 5-chloro-2-hydroxy-3((4-methoxyphenyl)diazenyl)benzyl methacrylate.

17. The ophthalmic device material according to claim 1, wherein the implant device material contains from 0.5 to 4% w/w of the UV/Vis absorber.

18. An ophthalmic device material according to claim 17, wherein the blue light chromophore is included in the ophthalmic device material at a concentration from 0.01 to 0.08% w/w.

19. The ophthalmic device material according to claim 1, the blue light chromophore is included in the ophthalmic device material at a concentration from 0.01 to 0.08% w/w.

* * * * *